United States Patent [19]

Gorman et al.

[11] Patent Number: 4,614,649

[45] Date of Patent: Sep. 30, 1986

[54] ANTIPLAQUE SACCHARIN SALT DENTRIFICES AND METHOD OF USE THEREOF

[75] Inventors: William G. Gorman, East Greenbush; Karl F. Popp, Schodack; Kenneth M. Mavica, East Greenbush, all of N.Y.

[73] Assignee: Sterling Drug Inc., New York, N.Y.

[21] Appl. No.: 560,059

[22] Filed: Dec. 9, 1983

[51] Int. Cl.$^4$ .............................................. A61K 7/22
[52] U.S. Cl. ........................................ 424/54; 424/49
[58] Field of Search ........................................... 424/54

[56] References Cited

U.S. PATENT DOCUMENTS

| | | | |
|---|---|---|---|
| 2,684,924 | 7/1954 | Rose et al. | 167/30 |
| 2,689,170 | 9/1954 | King | 424/56 |
| 2,725,326 | 11/1955 | Shibe et al. | 167/33 |
| 2,828,316 | 3/1958 | Pacini et al. | 260/301 |
| 3,133,072 | 5/1964 | Shibe et al. | 260/281 |
| 3,164,481 | 1/1965 | Shibe | 106/10 |
| 3,223,704 | 12/1965 | Shibe et al. | 424/54 |
| 3,249,497 | 5/1966 | Shibe et al. | 167/33 |
| 3,344,018 | 9/1967 | Shibe et al. | 424/54 |
| 3,468,898 | 9/1969 | Cutler et al. | 260/301 |
| 3,538,230 | 11/1970 | Pader et al. | 424/50 |
| 3,804,946 | 4/1974 | Harrison et al. | 424/54 |
| 3,842,168 | 10/1974 | Colodney | 424/52 |
| 3,843,779 | 10/1974 | Norfleet | 424/54 |
| 3,911,104 | 10/1975 | Harrison | 424/52 |
| 3,927,201 | 12/1975 | Baines et al. | 424/54 |
| 3,937,805 | 2/1976 | Harrison | 424/54 |
| 3,957,967 | 5/1976 | L'Orange | 424/49 |
| 3,976,765 | 8/1976 | Nachtigal | 424/54 |
| 3,984,537 | 10/1976 | Harrison et al. | 424/54 |
| 4,001,393 | 1/1977 | L'Orange | 424/54 |
| 4,022,834 | 5/1977 | Gundersen | 260/564 |
| 4,053,636 | 10/1977 | Eustis et al. | 424/326 |
| 4,130,636 | 12/1978 | Tomlinson | 424/52 |
| 4,157,387 | 6/1979 | Benedict | 424/49 |
| 4,206,215 | 6/1980 | Bailey | 424/263 |
| 4,254,101 | 3/1981 | Denny | 424/52 |
| 4,303,641 | 12/1981 | DeWolf et al. | 424/49 |

FOREIGN PATENT DOCUMENTS 384891 4/1963 Japan.
1066795 10/1963 United Kingdom.

OTHER PUBLICATIONS

Pacini et al., Chem. Abst. 52:14700b, (1958) of U.S. Pat. No. 2,828,316, Debittered Quaternary Compound of Benzethonium Chloride and Saccharin.
Sawyer et al., C.A. 64, #12955h (1966), of U.S. Pat. No. 3,236,666 (Better Bactericide).
Wm. J. Shibe (Hollichem Corp.), Chem. Abstr. 67, #47081a (1967), of Brit. No. 1,066,795 (1963) (Toothpowder, Toothpaste, Lozenges, and Mouthwash of Quaternary Ammonium Benzosulfimide).
Wm. J. Shibe, Chem. Abst. 62, #6687g (1965), of U.S. Pat. No. 3,164,481 (Qaternary Ammonium Benzosulfimides Have an Agreeable Taste So They May Be Used in Products Subject to Oral Use).
Wm. J. Shibe et al., Chem. Abst. 62, #4360b (1965) of Soap. Chem. Specialties 40(7):83-5,88-9, (1964), Quat. Amm. Saccharinates Are More Effective and Less Toxic.
Shibe, C.A. 65, #923d (1966), of U.S. Pat. No. 3,249,497 (1966).
USPTO-1878 Apr. 1985, Translation of Japan, Kokai 38-4891 (4-26-63), "A Method to Produce Bis-Biguanide Saccharin Salt", Sumitomo, Ltd.
Shibe et al., Soap. Chem. Specialties, 40(7): 83-85, 88-89 (1964), New Apporoach to Quaternary Ammonium Compounds.
Chemical Abstracts, vol. 59, p. 11333b, 1963: Abstract of Japanese Patent 4891 (1963).
The Merck Index, Ninth Edition, 1976, monographs 224, 1059, 1987, 2060, 2874 and 4205.
Disinfection, Sterilization and Preservation, Seymour S. Block, Editor, 2nd Edition, Lea & Febiger, Philadelphia, 1977, pp. 325–347, chapter by A. N. Petrocci.

*Primary Examiner*—Shep K. Rose
*Attorney, Agent, or Firm*—Theodore C. Miller; Paul E. Dupont; B. Woodrow Wyatt

[57] ABSTRACT

Antiplaque dentifrices containing as the antiplaque ingredient the saccharin salt of an amino or quaternary ammonium antimicrobial agent, particularly chlorhexidine saccharin salt or octenidine saccharin salt, and the method of inhibiting, reducing and preventing dental plaque therewith are disclosed.

10 Claims, No Drawings

ANTIPLAQUE SACCHARIN SALT DENTRIFICES AND METHOD OF USE THEREOF

BACKGROUND OF THE INVENTION

1. Field of the Invention

The invention relates to antiplaque dentifrices containing as the antiplaque ingredient the saccharin salt of an amino or quaternary ammonium antimicrobial agent and to the method of inhibiting, reducing and preventing dental plaque therewith.

2. Information Disclosure Statement

Rose et al. U.S. Pat. No. 2,684,924 issued July 27, 1954 describes antimicrobial aryl bisbiguanides including chlorhexidine (The Merck Index, Ninth Edition, 1976, monograph 2060).

Chemical Abstracts (vol. 59, p. 11333b, 1963) sets forth an abstract of Japanese Pat. No. 4891 (1963) describing bis(p-chlorophenylbiguanido)hexane saccharinate, which is the saccharin salt of chlorhexidine.

Eustis et al. U.S. Pat. No. 4,053,636 issued Oct. 11, 1977 describes antimicrobial dichlorocyclopropylphenyl bisbiguanides.

Cutler et al. U.S. Pat. No. 3,468,898 issued Sept. 23, 1969 describes antimicrobial alkyl bisbiguanides including alexidine, which is shown by The Merck Index cited above (monograph 224).

Gundersen U.S. Pat. No. 4,022,834 issued May 10, 1977 describes antimicrobial cycloalkyl bisbiguanides.

Petrocci (chapter entitled "Quaternary Ammonium Compounds" in Disinfection, Sterlization, and Preservation, Seymour S. Block, Editor, 2nd Edition, Lea & Febiger, Philadelphia, 1977, pp. 325-347) describes the quaternary ammonium disinfectants, which are a well-known class of antimicrobial agents. Particularly well-known examples shown by The Merck Index cited above are benzalkonium chloride (monograph 1059), benzethonium chloride (monograph 1078), cetylpyridinium chloride (monograph 1987) and dequalinium chloride (mongraph 2874).

Bailey U.S. Pat. No. 4,206,215 issued June 3, 1980 describes antimicrobial bis[4-(substituted-amino)-1-pyridinium]alkane salts and the dental plaque preventing method of use of certain species thereof.

Pader et al. U.S. Pat. No. 3,538,230 issued Nov. 3, 1970 describes dentifrices containing silica erogels as cleaning and polishing agents.

DeWolf et al. U.S. Pat. No. 4,303,641 issued Dec. 1, 1981 describes dentifrices containing hydrous silica gels as cleaning and polishing agents.

King U.S. Pat. No. 2,689,170 issued Sept. 14, 1954 describes dentifrices containing higher alkanoylaminoalkanecarboxylic acids and salts thereof, especially sodium N-lauroyl sarcoside (sarcosinate) as caries inhibiting agents. Monograph 4205 of The Merck Index cited above describes sodium N-lauroyl sarcosinate (Gardol ®) as being useful as a detergent, foaming agent and antienzyme for dentifrices.

Attempts have been made to formulate antiplaque dentifrices and one such product is CORSODYL ™ Dental Gel containing 1% by weight of chlorhexidine gluconate (manufactured by Imperial Chemical Industries Limited, Pharmaceuticals Division, Macclesfield, Cheshire, England), but these attempts including CORSODYL ™ Dental Gel have been generally unsuccessful due to the problem of combining antiplaque activity, good taste, good foaming ability and good polishing ability in a single formulation. The presently described and claimed invention overcomes this problem and provides such a formulation.

SUMMARY OF THE INVENTION

In a composition of matter aspect the invention is an antiplaque dentifrice comprising (A) an effective dental plaque inhibiting, reducing or preventing amount of the saccharin salt of an amino or quaternary ammonium antimicrobial agent selected from the group consisting of (a) a compound having the structural formula

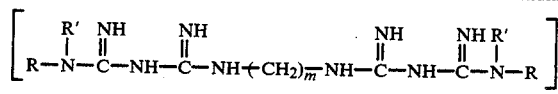

Formula I

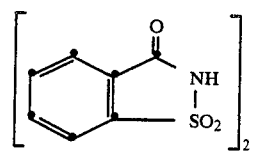

wherein R taken alone is phenyl substituted by alkyl, alkoxy, nitro or halo, p-(2,2-dichlorocyclopropyl)phenyl, alkyl having from 6 to 16 carbon atoms, cycloalkyl or polycyclic alkyl having 5 or more carbon atoms or lower-alkylcycloalkyl or cycloalkyl-lower-alkyl having from 1 to 4 carbon atoms in lower alkyl; R' taken alone is hydrogen; R and R' taken together are 3-azabicyclo(3,2,2)nonyl; and n is an integer from 3 to 9;

(b) a compound having the structural formula

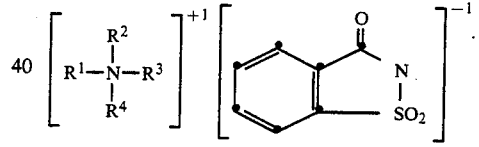

Formula II or

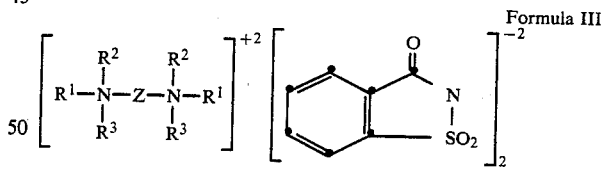

Formula III wherein $R^1$ is long-chain alkyl or aralkyl; $R^2$ is short-chain alkyl, long-chain alkyl or aralkyl, benzly or part of an aromatic system or non-aromatic system; $R^3$ and $R^4$ are short-chain alkyl or part of an aromatic ring system or non-aromatic ring system; and Z is a carbon-hydrogen chain; and (c) a compound having the structural formula

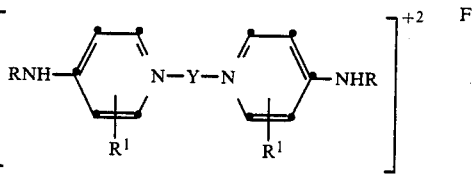

Formula IV

-continued

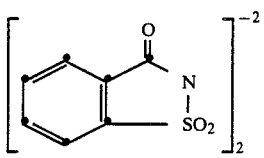

wherein Y is alkylene containing from 4 to 18 carbon atoms and separating the two 4-(R-amino)-1-pyridinium groups by from 4 to 18 carbon atoms; R is the same in both occurrences and is alkyl containing from 6 to 18 carbon atoms, cycloalkyl containing from 5 to 7 carbon atoms, benzyl or phenyl substituted by methylenedioxy or one or two substituents selected from the group consisting of halo, lower-alkyl, lower alkoxy, nitro, cyano and trifluoromethyl; and $R_1$ is the same in both occurrences and is hydrogen or lower-alkyl;

(B) a polishing agent or thickening agent selected from the group consisting of silicon dioxide, silicic acid, silica, amorphous silica, precipitated silica, hydrated silica, silica hydrate, silica gel, silica xerogel and hydrous silica gel; and (C) a foaming agent selected from the group consisting of N-alkanoylsarcosine or N-alkenoylsarcosine or an alkali metal, ammonium or alkanolamine salt thereof, wherein alkanoyl or alkenoyl has from 8 to 18 carbon atoms and alkanolamine has from 2 to 9 carbon atoms.

In a process aspect the invention is the method of inhibiting, reducing or preventing dental plaque which comprises contacting the dental plaque itself or the natural or artifical teeth or oral cavity of a living person with an effective dental plaque inhibiting, reducing or preventing amount of the above-described antiplaque dentifrice.

DETAILED DESCRIPTION OF THE INVENTION INCLUSIVE OF THE PREFERRED EMBODIMENTS

The Compositions

The non-saccharin salts corresponding to the compounds of Formulas I-IV are generally and particularly described by the above-cited prior art, which in some instances also describes the saccharin salts. Those saccharin salts of Formulas I-IV which are not described by the prior art are prepared by reacting in an aqueous solvent a corresponding relatively soluble non-saccharin salt with saccharin or a soluble salt of saccharin and separating the relatively insoluble saccharin salt.

The aqueous solvent can be water alone, which is the preferred solvent, or a mixture of water and one or more water-miscible organic solvents selected from the alcohols, ketones, acids, amides, nitriles and sulfoxides and multifunctional and mixed functional solvents. Since saccharin is only slightly soluble in water, a soluble salt, for example, an alkali metal salt, is preferably used. Saccharin sodium salt is most preferred. The reaction is preferably carried out at a temperature in the range of 0°-100° C., most preferably 20°-60° C.

A preferred saccharin salt of Formulas I-IV is the compound of Formula I wherein R is p-chlorophenyl, R' is hydrogen and n is 6, which is the saccharin salt of chlorhexidine and is described by the above-cited Chemical Abstracts abstract of Japanese Pat. No. 4891. Another preferred saccharin salt of Formulas I-IV is the compound of Formula IV wherein R is octyl, $R_1$ is hydrogen and Y is 1,10-decylene, which is the saccharin salt of octenidine and is prepared from molar equivalent quantities of octenidine dihydrochloride salt and saccharin sodium salt in water (m.p. 82° C.).

The effective dental plaque inhibiting, reducing or preventing amount of the saccharin salt of Formulas I-IV is generally in the range of 0.1-10% and most generally of the order of 1% by weight of the dentifrice.

Silicic acid, silica, amorphous silica, precipitated silica, hydrated silica, silica hydrate, silica gel, silica xerogel and hydrous silica gel are all forms of silicon dioxide ($SiO_2$) differing in the method of formation and extent of hydration. Of these hydrous silica gel (hydrated silica) is most preferred. Different grades of hydrated silica are available for polishing and thickening. The dentifrices of the invention preferably contain both a polishing grade and a thickening grade of hydrated silica. The amount of polishing agent and thickening agent is generally in the range of 5-50% by weight of the dentifrice.

In N-alkanoylsarcosine and N-alkenoylsarcosine alkanoyl and alkenoyl having from 8 to 18 carbon atoms can be branched or unbranched. Unbranched alkanoyl having an even number of carbon atoms is preferred, especially lauroyl having 12 carbon atoms. Preferred alkanolamine salts include the monoethanolamine, diethanolamine and triethanolamine salts. The alkali metal salts include the lithium, sodium and potassium salts. Sodium salts are preferred. The most preferred foaming agent is sodium N-lauroyl sarcosinate. The amount of foaming agent is generally in the range of 0.1-10% and most generally of the order of 1% by weight of the dentifrice.

In addition to the above-described components the dentifrices of the invention generally also contain one or more humectants, for example, sorbitol, glycerin or a polyethylene glycol, for example, PEG-6-32, which is an adopted name for a mixture of the polyethylene glycol having 6 ethylene oxide units and the polyethylene glycol having 32 ethylene glycol units; caries reducing, inhibiting or preventing fluoride salts, for example, sodium fluoride, sodium monofluorophosphate or stannous fluoride; sweeteners, for example, free saccharin in addition to the bound saccharin of the above-described saccharin salts, cyclamate or aspartame; flavors; colorants; acids or bases to adjust the pH (desirably about 7), for example, hydrochloric acid or sodium hydroxide; and water.

In preparing the dentifrices of the invention the saccharin salts of Formulas I-IV can be formed in situ, but use of preformed saccharin salt is preferred. To ensure maximum possible antiplaque effect the preformed saccharin salt is added as the last ingredient of the dentifrice formulation. A typical order of addition of the remaining ingredients of a typical formulation is: water, fluoride salt, humectants, sweetener, foaming agent, flavors, colorant, acid or base to adjust pH, and polishing and thickening agents. Accordingly the following examples were prepared.

EXAMPLE 1

| Ingredient | Percent by Weight |
| --- | --- |
| Chlorhexidine Saccharin Salt | 1.10 |
| Sodium Fluoride | 0.220 |
| Sorbitol Solution | 46.3 |
| Hydrated Silica, Polishing Grade | 17.0 |
| Glycerin | 15.0 |
| Hydrated Silica, Thickening Grade | 11.1 |

-continued

| Ingredient | Percent by Weight |
|---|---|
| PEG-6-32 | 3.00 |
| Sodium Lauroyl Sarcosinate | 2.10 |
| Flavors | 1.100 |
| Saccharin | 0.100 |
| Colorants | 0.002500 |
| Hydrochloric Acid to make pH 7 | — |
| Purified Water to make | 100.0 |

EXAMPLE 2

| Ingredient | Percent by Weight |
|---|---|
| Octenidine Saccharin Salt | 1.10 |
| Sodium Fluoride | 0.220 |
| Sorbitol Solution | 46.3 |
| Hydrated Silica, Polishing Grade | 17.0 |
| Glycerin | 15.0 |
| Hydrated Silica, Thickening Grade | 11.1 |
| PEG-6-32 | 3.00 |
| Sodium Lauroyl Sarcosinate | 2.10 |
| Flavors | 1.100 |
| Saccharin | 0.100 |
| Colorant | 0.00400 |
| Hydrochloric Acid to make pH 7 | — |
| Purified Water to make | 100.0 |

Antiplaque Properties of the Compositions

An in vitro test for effect of the foregoing compositions against preformed dental plaque was carried out.

*Streptococcus mutans* NCTC 10449, *Streptococcus sanguis* ATCC 10558 and *Actinomyces viscosus* M-100 were used as plaque forming microorganisms and were stored prior to use in a frozen or lyophilized state. Working stock cultures were maintained by twice monthly passage in fluid thioglycollate medium containing 20% (w/v) meat extract and excess calcium carbonate. For plaque formation the medium of Jordan et al. (J. Dent. Res., vol. 39, pp. 116–123, 1960) supplemented with 5% (w/v) sucrose was used. All cultures were adapted to this growth medium by at least one growth cycle prior to use in the tests.

The substrates were cleaned, sterilized ceramic hydroxylapatite (durapatite) slabs approximately $\frac{1}{4}'' \times \frac{1}{2}'' \times 2''$ in size, which were manipulated during transfer and brushing with sterile clamps (hemostats). Brushing was done with a wetted medium bristle toothbrush and one inch strips of the dentifrice on all sides of the slab for one minute. The slab was then rinsed in running tap water for one minute with manipulation to ensure removal of all visible dentifrice.

Plaques were developed on the slabs by daily passage through the supplemented Jordan et al. medium (20 ml.) in culture tubes. Only the initial culture tube was inoculated with the plaque-forming microorganism (at least 0.3 ml. of a late log-phase culture). Subsequent tubes were not directly inoculated. Thus, only the most adherent microorganisms were carried over, thereby permitting formation of strongly adherent plaques. After three successive daily transfers the slabs were brushed with the dentifrice, rinsed and immersed in fresh growth medium containing a pH indicator (bromocresol purple). The culture tubes were incubated for 24 hours at 37° C. under an anaerobic atmosphere. A once daily brushing regimen was thus simulated. Alternatively the slabs were brushed twice daily and the incubation periods were 6 and 16 hours in duration. Growth and metabolic activity (acid production) were subsequently assessed, and the treatment and incubation(s) were repeated. The slabs were brushed daily until the cultures failed to yield acid end products and (ideally) yielded viable bacteria.

Metabolic activity (M.A.) was measured 12 and 36 hours after final treatment and scored +(acid production and turbidity increase), ±(no acid shift but noticeable turbidity increase) or ∓(no acid shift and minimal evidence of turbidity increase). Plaque was measured following staining with erythrosin and scored 0, 1, 2, 3, 4 or Fl (flecks or microcolonies). The following results were obtained from duplicate brushings twice daily for three successive days with only water and no dentifrice, a placebo dentifrice (the composition of Examples 1 and 2 wherein the antimicrobial agent was replaced by an equal amount of sorbitol solution) and the compositions of Examples 1 and 2.

| Com- position | Measurement | Score S. Mutans 10449 | S. Sanguis 10558 | A. Viscosus M-100 |
|---|---|---|---|---|
| Water | 12-Hr. M.A. | +, + | +, + | ±, ± |
|  | 36-Hr. M.A. | +, + | +, + | +, + |
|  | Plaque | 3, 3 | 4, 4 | 3, 4 |
| Placebo | 12-Hr. M.A. | +, ± | +, ± | ∓, ∓ |
|  | 36-Hr. M.A. | +, + | +, ± | ±, ± |
|  | Plaque | 1, 1 | 1, 1 | 1, ½ |
| Example 1 | 12-Hr. M.A. | ∓, ∓ | ∓, ∓ | ∓, ∓ |
|  | 36-Hr. M.A. | ∓, ± | +, ± | ∓, ∓ |
|  | Plaque | Fl, Fl | ½, Fl | Fl, Fl |
| Example 2 | 12-Hr. M.A. | ∓, ∓ | ∓, ± | ∓, ∓ |
|  | 36-Hr. M.A. | ∓, ∓ | ±, + | ∓, ∓ |
|  | Plaque | Fl, Fl | Fl, Fl | Fl, Fl |

Comparative Tests

As stated above previous attempts including CORSODYL ™ Dental Gel to combine antiplaque activity, good taste, good foaming ability and good polishing ability in a single dentifrice formulation have been generally unsuccessful. Although CORSODYL ™ Dental Gel showed good antiplaque activity against preformed *S. mutans* plaque on durapatite slabs in vitro after one brushing per day on three successive days, it does not have the other three attributes in good measure when compared with the dentifrice of Example 1.

Comparison of the taste of the dentifrice of Example 1 with that of CORSODYL ™ Dental Gel showed that CORSODYL ™ Dental Gel had a bitter taste whereas the dentifrice of Example 1 did not have a bitter taste.

The following test was carried out to compare the foaming ability of the dentifrice of Example 1 with that of CORSODYL ™ Dental Gel. Each of the test formulations (0.5 g.) was placed in a 50-ml. graduate cylinder together with human salvia which had been passed through a 100-mesh screen (10 ml.) and a toothbrush whose handle had been cut off so that it would fit into the cylinder (Abco Dealers Inc. #350100 cut to a length of 1½ inches). More saliva was added to make the total volume 20 ml. The cylinder was securely stoppered and rotated end over end at a constant rate of about 34 revolutions per minute. Foam volumes were read after 25, 50, 75 and 100 revolutions. Seven cylinders were used and mean foam volumes and standard errors were calculated for each formulation. The following results were obtained.

| Number of Revolutions | Mean Foam Volume (ml.) | |
|---|---|---|
| | CORSODYL ™ Dental Gel | Dentifrice of Example 1 |
| 25 | 20 ± 0.2 | 22 ± 0.3 |
| 50 | 21 ± 0 | 24 ± 0.3 |
| 75 | 22 ± 0.2 | 25 ± 0.3 |
| 100 | 22 ± 0 | 26 ± 0.3 |
| Overall Mean | 21 ± 0.1 | 24 ± 0.3 |

The mean foam volume values for the dentifrice of Example 1 are significantly greater than those of CORSODYL ™ Dental Gel (p=0.05).

Due to the presence of the polishing agent the dentifrices of the invention have good polishing ability. CORSODYL ™ Dental Gel, on the other hand, appears to contain little or no polishing agent and thus to have little or no polishing ability. This is shown by the fact that CORSODYL ™ Dental Gel has a very small residue after combustion (0.05%, 0.06% in two determinations) compared with the dentifrices of Example 1 (19.9%) and Example 2 (19.3%).

We claim:

1. An antiplaque dentifrice comprising
   (A) an effective dental plaque inhibiting, reducing or preventing amount of a compound having the structural formula

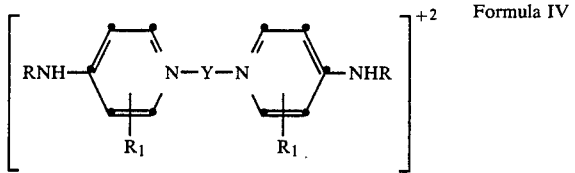

Formula IV wherein Y is alkylene containing from 4 to 18 carbon atoms and separating the two 4-(R-amino)-1-pyridinium groups by from 4 to 18 carbon atoms; R is the same in both occurrences and is alkyl containing from 6 to 18 carbon atoms, cycloalkyl containing from 5 to 7 carbon atoms, benzyl or phenyl substituted by methylenedioxy or one or two substituents selected from the group consisting of halo, lower-alkyl, lower-alkoxy, nitro, cyano and trifluoromethyl; and $R_1$ is the same in both occurrences and is hydrogen or lower-alkyl;
   (B) a polishing agent or thickening agent selected from the group consisting of silicon dioxide, silicic acid silica, amorphous silica, precipitated silica, hydrated silica, silica hydrate, silica gel, silica xerogel and hydrous silica gel; and

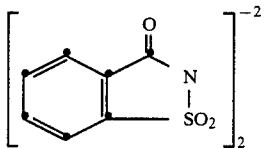

(C) a foaming agent selected from the group consisting of N-alkanoylsarcosine or N-alkenoylsarcosine or an alkali metal, ammonium or alkanolamine salt thereof, wherein alkanoyl or alkenoyl has from 8 to 18 carbon atoms and alkanol has from 2 to 3 carbon atoms.

2. An antiplaque dentifrice according to claim 1 wherein in the compound of Formula IV R is octyl, $R_1$ is hydrogen and Y is 1,10-decylene.

3. An antiplaque dentifrice according to claim 2 which comprises both a polishing agent and a thickening agent.

4. An antiplaque dentifrice according to claim 3 wherein the polishing agent and the thickening agent are both hydrous silica gels.

5. An antiplaque dentifrice according to claim 4 wherein the foaming agent is sodium lauroyl sarcosinate.

6. The method of inhibiting, reducing or preventing dental plaque which comprises contacting the dental plaque itself or the natural or artificial teeth or oral cavity of a living person with an effective dental plaque inhibiting, reducing or preventing amount of an antiplaque dentifrice according to claim 1.

7. An antiplaque dentifrice comprinsing from about 0.1% to about 10% of octenidine saccharin salt, a total from about 5% to about 50% of a polishing grade of hydrous silica gel and a thickening grade of hydrous silica gel, and from about 0.1% to about 10% of sodium lauroyl sarcosinate.

8. An antiplaque dentifrice comprising about 1% octenidine saccharin salt, about 17% of the polishing grade of hydrous silica gel, about 11% of the thickening grade of hydrous silica gel, and about 2% of sodium lauroyl sarcosinate according to claim 7.

9. The method of inhibiting, reducing or preventing dental plaque which comprises contacting the dental plaque itself or the natural or artificial teeth or oral cavity of a living person with an effective dental plaque inhibiting, reducing or preventing amount of an antiplaque dentifrice according to claim 7.

10. The method of inhibiting, reducing or preventing dental plaque which comprises contacting the dental plaque itself or the natural or artificial teeth or oral cavity of a living person with an effective dental plaque inhibiting, reducing or preventing amount of an antiplaque dentifrice according to claim 8.

* * * * *